(12) United States Patent
Yeh et al.

(10) Patent No.: US 8,950,240 B2
(45) Date of Patent: Feb. 10, 2015

(54) ACETONE GAS SENSOR APPARATUS

(75) Inventors: Jer-Liang Andrew Yeh, Taichung (TW); Shang-Jr Gwo, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 81 days.

(21) Appl. No.: 13/432,108

(22) Filed: Mar. 28, 2012

(65) Prior Publication Data

US 2013/0259748 A1 Oct. 3, 2013

(51) Int. Cl.
*G01N 33/497* (2006.01)
*G01N 27/00* (2006.01)
*G01N 1/22* (2006.01)

(52) U.S. Cl.
USPC ............ 73/31.06; 73/23.2; 73/23.3; 73/31.05; 257/252; 257/253; 257/414; 422/83; 422/84; 422/98; 438/48; 438/49

(58) Field of Classification Search
USPC ............ 73/23.2, 23.3, 31.05, 31.06; 257/252, 257/253, 414; 422/82, 83, 98; 438/48, 49
See application file for complete search history.

(56) References Cited

U.S. PATENT DOCUMENTS 6,467,333 B2 * 10/2002 Lewis et al. ............... 73/31.05

OTHER PUBLICATIONS

Chang et al., Highly sensitive hydrogen detection using a Pt-catalyzed InN epilayer, Applied Physics Express 3 (2010) 114101.*
Sundgren, H., et al. "Artificial neural networks and gas sensor arrays: quantification of individual components in a gas mixture." Measurement Science and Technology 2.5 (1991): 464.*

* cited by examiner

*Primary Examiner* — In Suk Bullock
*Assistant Examiner* — Robert Eom
(74) *Attorney, Agent, or Firm* — The Weintraub Group, P.L.C.

(57) ABSTRACT

An acetone gas sensor apparatus, including: a chamber, used for containing a gas sample taken from a breath of a person; and an acetone gas sensor, placed in the chamber for generating an output current in response to an acetone concentration of the gas sample, the acetone gas sensor including: a substrate; a buffer layer, deposited on the substrate; an InN epilayer, deposited on the buffer layer for providing a current path for the output current; a first conductive contact, deposited on the InN epilayer for providing a drain contact; and a second conductive contact, deposited on the InN epilayer for providing a source contact.

17 Claims, 6 Drawing Sheets

ACETONE GAS SENSOR APPARATUS

BACKGROUND OF THE INVENTION

1. Field of the Invention

The present invention relates to acetone gas sensor apparatuses, and more particularly to acetone gas sensor apparatuses capable of detecting acetone in a gas sample with low acetone concentrations.

2. Description of the Related Art

Over two hundred kinds of volatile organic compounds (VOCs) are found in the human breath and the concentrations of such VOCs are usually measured to be at sub-ppm levels or even lower for healthy human beings. Abnormal concentrations of the breath VOCs are reported to correlate with unhealthy/injurious body/organ conditions; for instance, acetone gas for diabetes, trimethylamine for uremic patients and ammonia gas for renal disease. Hence, the VOCs in the human breath can be potentially applied as disease-specific biomarkers for non-invasive early detection or monitoring of a variety of diseases.

Acetone could be produced via the fatty acid oxidation in human bodies. Excessive acetone circulating in the blood systems is excreted from the lungs. Higher acetone concentrations ranging from 1.7 ppm to 3.7 ppm could be detected in breath for those who are diabetic, while the breath from a healthy person is typically less than 0.8 ppm. Therefore, gas sensors with the capacity of sub-ppm acetone detection play an important role on the development of non-invasive monitoring or diagnosis of potential diabetic patients.

U.S. Pat. No. 6,454,723 discloses a metabolic fitness training apparatus which measures the concentration of acetone in a trainer's breath while exercising. The metabolic fitness training apparatus include a housing, an acetone sensitive sensor, an optical detection circuit, and a mouthpiece attached to the housing. The sensor contains reagents such as salicylaldehyde or derivatives thereof which react with acetone to change the optical transparency of the sensor. The optical detection circuit may include a LED and a photodetector or a photometric instrument to measure the change in optical transparency of the sensor, and convert that change to acetone concentration. There may also be a display for viewing the acetone concentration.

U.S. Pat. No. 7,417,730 discloses an apparatus and method for monitoring diabetes through breath acetone detection and quantification that employs a microplasma source in combination with a spectrometer. The microplasma source provides sufficient energy to produce excited acetone fragments from the breath gas that emit light. The emitted light is sent to the spectrometer, which generates an emission spectrum that is used to detect and quantify acetone in the breath gas.

However, both the apparatus of U.S. Pat. No. 6,454,723 and the apparatus of U.S. Pat. No. 7,417,730 have the disadvantages of being expensive and not compact enough.

Meanwhile, there are table-top equipments, such as Gas Chromatography-Mass Spectrometry (GC-MS) or Proton Transfer Reaction-Mass Spectrometry (PTR-MS) for detecting the sub-ppm traces of the VOCs. However, such equipments do not meet the requirements of clinical or at-home applications, including portability, small form factor, cost-effective performance, real-time analysis and so forth.

Still, there are alternative sensors for detecting gas traces with low concentrations, including electrochemical sensors, surface acoustic wave sensors, quartz crystal microbalance sensors, and semiconductor gas sensors. Among them, gas sensors are developed on semiconductor materials, viewed as electronic devices, and capable of being further integrated with electronic circuitries.

Table 1 shows the comparison of various gateless (i.e. unbiased) acetone gas sensors that are made on metal oxides or on metal nitrides. Metal oxide materials, such as $LaFeO_3$, $In_2O_3$, $WO_3$ and ZnO, were demonstrated, but majority of them cannot achieve sub-ppm acetone detection with high sensitivity and high linearity.

TABLE 1

List of acetone gas sensors

| Material | Principle of operation Device type | Sensitivity (% per conc. decade change) | Lowest Concentration Detected | Response time | Operation temperature |
|---|---|---|---|---|---|
| $In_2O_3$ | Resistance (voltage) change Nanowire | 0.6 | 25 ppm | ~10 sec | 400° C. |
| $WO_3$ | Resistance (voltage) change Nanoparticle | 1.5 | 0.2 ppm | ~3.5 min | 400° C. |
| ZnO | Resistance (voltage) change Thin Film | 5.71 | 100 ppm | 30 sec | 200° C. |
| $LaFeO_3$ | Resistance (voltage) change Thin Film | 0.7 | 500 ppm | 33 sec | 275° C. |
| GaN | Resistance (voltage) change Thin Films | ~23 | 500 ppm | 10 sec for 1000 ppm | 350° C. |

To solve the foregoing problems, a novel sensor apparatus, which is compact, portable, inexpensive, and capable of detecting low acetone concentrations in a breath sample, is therefore needed.

SUMMARY OF THE INVENTION

One objective of the present invention is to provide an acetone gas sensor apparatus, which is capable of detecting acetone in a gas sample with low acetone concentrations.

Another objective of the present invention is to provide an acetone gas sensor apparatus, which is capable of speeding up the acetone detection process.

Still another objective of the present invention is to provide an acetone gas sensor apparatus, which is portable and easy to implement.

To achieve the foregoing objectives, an acetone gas sensor apparatus is proposed, comprising:

a chamber, used for containing a gas sample taken from a breath of a person;

an acetone gas sensor, placed in the chamber for generating an output current in response to an acetone concentration of the gas sample;

a heating device, used for heating the acetone gas sensor; and a measurement unit, coupled with the acetone gas sensor for providing a measured signal corresponding to the output current;

wherein said acetone gas sensor comprising:

a substrate;

a buffer layer, deposited on the substrate;

an InN epilayer, deposited on the buffer layer for providing a current path for the output current;

a first conductive contact, deposited on the InN epilayer for providing a drain contact, which is coupled to a first voltage;

a second conductive contact, deposited on the InN epilayer for providing a source contact, which is coupled to a second voltage; and a catalytic layer, which is deposited, between the first conductive contact and the second conductive contact, on the InN epilayer.

After measurement, if the measured signal is below a first level, the person is diagnosed as normal; and when the measured signal is above a second level, which is higher than the first level, the person is diagnosed with diabetes.

Preferably, the substrate is a c-plane sapphire layer.

Preferably, the buffer layer is an AlN layer.

Preferably, the first conductive contact and the second conductive contact are made of metal.

Preferably, the first conductive contact and the second conductive contact include a structure of Au/Al/Ti.

Preferably, the catalytic layer includes platinum.

Preferably, the heating device is placed underneath the acetone gas sensor.

Preferably, the heating device is an aluminum heater.

To make it easier for our examiner to understand the objective of the invention, its structure, innovative features, and performance, we use preferred embodiments together with the accompanying drawings for the detailed description of the invention.

DETAILED DESCRIPTION OF THE PREFERRED EMBODIMENTS

The present invention will be described in more detail hereinafter with reference to the accompanying drawings that show the preferred embodiment of the invention.

Figure 1:
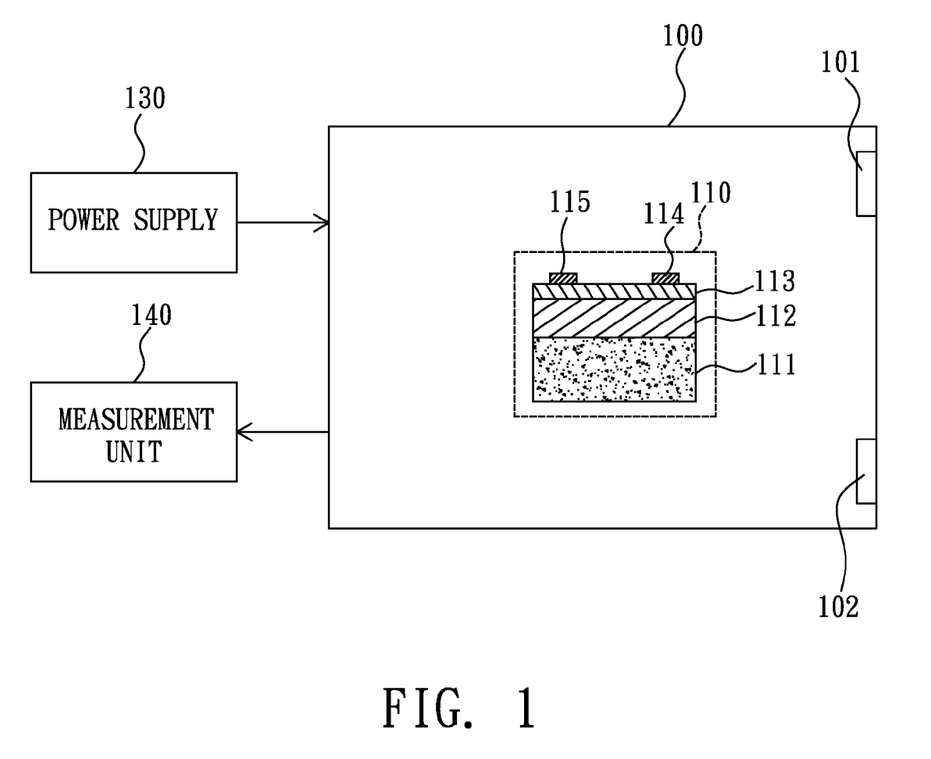
FIG. 1 is an illustrative diagram for an acetone gas sensor apparatus according to a preferred embodiment of the present invention.

Please refer to FIG. 1, which illustrates an acetone ($CH_3COCH_3$) gas sensor apparatus according to a preferred embodiment of the present invention. As illustrated in FIG. 1, the acetone gas sensor apparatus mainly includes a chamber 100, and an acetone gas sensor 110. The acetone gas sensor apparatus is powered by a power supply 130, and the measurement result is derived by a measurement unit 140.

The chamber 100 has an inlet 101 for the inflow of a breath gas, and an outlet 102 for the outflow of the gas in the chamber 100.

The acetone gas sensor 110 includes a substrate layer 111, a buffer layer 112, an InN epilayer 113, a first conductive contact 114, and a second conductive contact 115.

The substrate layer 111, preferably a c-plane sapphire layer or a (111) silicon layer having a robust surface against chemical damages, is used for depositing a gateless transistor.

The buffer layer 112, preferably an AlN (aluminum nitride) layer, is deposited on the substrate layer 111 by using a plasma-assisted molecular beam epitaxy (PAMBE) system.

The InN (indium nitride) epilayer 113, deposited on the buffer layer 112 by using a plasma-assisted molecular beam epitaxy (PAMBE) system, is used for providing a current path between the first conductive contact 114 and the second conductive contact 115 for an output current. The InN epilayer 113 can provide a surface channel, which is an ultrathin n type channel of only few nanometers near the surface of the InN epilayer 113, formed due to surface electron inversion caused by acetone gas. The InN (indium nitride) epilayer 113 preferably has a thickness of around 10 nm. The InN epilayer 113 has excellent sensitivity to acetone gas due to its natural electronic characteristics, which include: a narrow band gap, excellent electron transport characteristics (mobility>1000 $cm^2/V \cdot s$), a high background electron density (typically in excess of $1 \times 10^{18}$ $cm^{-3}$), and unusual phenomenon of strong surface electron (charge) accumulation ($1.57 \times 10^{13}$ $cm^{-2}$). The surface electron accumulation along with the high mobility induces a large shift of the output current in response to a small concentration variation of an acetone gas environment. The excessive surface electrons are typically manifested by a high sheet density on the region within 5 nm away from the surface of the InN epilayer 113. Thus, the InN epilayer 113 is preferably formed to have a thickness of about 10 nm. By this arrangement, a surface charge accumulation layer will be formed to have a natural two-dimensional electron gas (2DEG) on its surface to facilitate acetone detection. In addition, InN is a chemically stable semiconductor with great resistance either to strong acids or to strong bases.

The output current of the InN epilayer 113 increases with acetone concentration and the principle is specified as follows.

First, acetone molecules can take away the pre-adsorbed oxygen atoms from the InN epilayer 113.

Secondly, the pre-adsorbed oxygen atoms on the InN epilayer 113 tend to become negatively charged (i.e. acceptors) due to a charge transferring process from a surface conduction band to the pre-adsorbed oxygen atoms.

Thirdly, the charge transferring process results in the formation of surface depletion layers, which reduce the surface conductivity of the InN epilayer 113.

Fourthly, when acetone ($CH_3COCH_3$) molecules are introduced to the acetone gas sensor apparatus, the hydrogen atoms on dissociated acetone molecules will react with the pre-adsorbed oxygen atoms to reduce the surface depletion layers. In addition, acetone molecules will be adsorbed onto the InN epilayer 113. As a result, both the reduction of the pre-adsorbed oxygen atoms and the adsorption of acetone molecules contribute electrons in the current channel, and the surface conductivity of the InN is increased accordingly.

The first conductive contact 114, deposited on the InN epilayer 113 by using an electron-beam evaporation system, is preferably a structure of Au/Al/Ti (50 nm/200 nm/50 nm) and serves as a drain terminal for coupling to a first voltage.

The second conductive contact 115, deposited on the InN epilayer 113 by using an electron-beam evaporation system, is preferably a structure of Au/Al/Ti (50 nm/200 nm/50 nm) and serves as a source terminal for coupling to a second voltage, wherein the second voltage is lower than the first voltage.

The power supply 130 is used for providing the first voltage and the second voltage.

The measurement unit 140 is used for measuring the output current.

Figure 2:
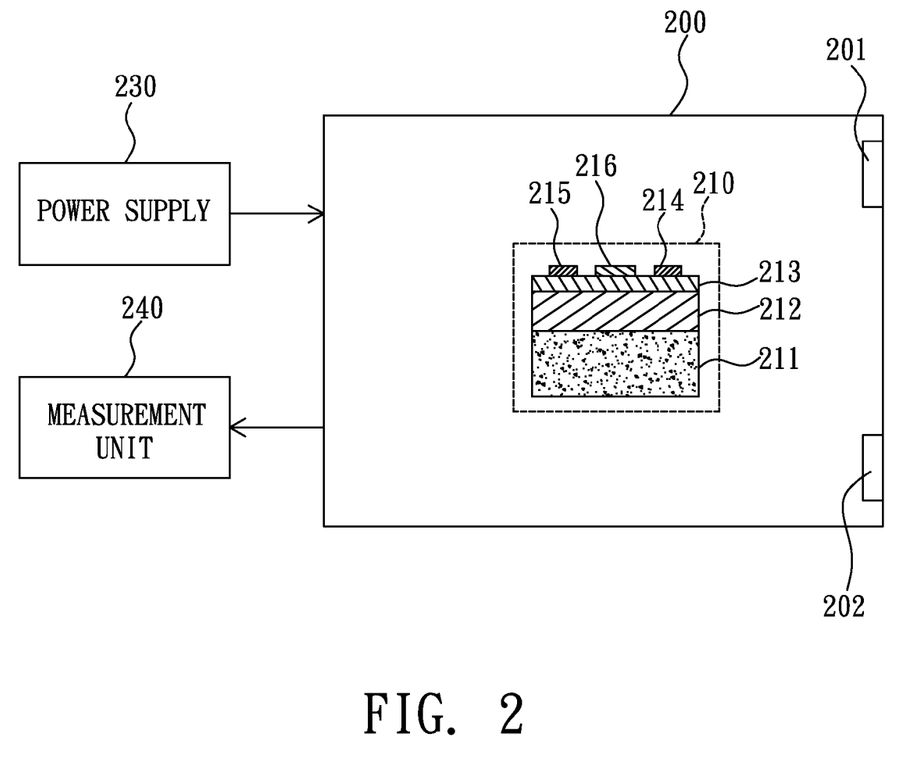
FIG. 2 is an illustrative diagram for an acetone gas sensor apparatus according to another preferred embodiment of the present invention.

Please refer to FIG. 2, which illustrates an acetone gas sensor apparatus according to another preferred embodiment of the present invention. As illustrated in FIG. 2, the acetone gas sensor apparatus mainly includes a chamber 200, and an acetone gas sensor 210, and the acetone gas sensor apparatus is powered by a power supply 230 and the measurement result is derived by a measurement unit 240.

The chamber 200 has an inlet 201 for the inflow of a breath gas, and an outlet 202 for the outflow of the gas in the chamber 200.

The acetone gas sensor 210 includes a substrate layer 211, a buffer layer 212, an InN epilayer 213, a first conductive contact 214, a second conductive contact 215, and a catalytic layer 216.

The substrate layer 211, preferably a c-plane sapphire layer or a (111) silicon layer having a robust surface against chemical damages, is used for depositing a gateless transistor.

The buffer layer 212, preferably an AlN layer, is deposited on the substrate layer 211 by using a plasma-assisted molecular beam epitaxy (PAMBE) system.

The InN epilayer 213, deposited on the buffer layer 212 by using a plasma-assisted molecular beam epitaxy (PAMBE) system, is used for providing a current path between the first conductive contact 214 and the second conductive contact 215 for an output current. The InN epilayer 213 can provide a surface channel, which is an ultrathin n type channel of only few nanometers near the surface of the InN epilayer 213, formed due to surface electron inversion caused by acetone gas. The InN (indium nitride) epilayer 213 preferably has a thickness of around 10 nm.

The first conductive contact 214, deposited on the InN epilayer 213 by using an electron-beam evaporation system, is preferably a structure of Au/Al/Ti (50 nm/200 nm/50 nm) and serves as a drain terminal for coupling to a first voltage.

The second conductive contact 215, deposited on the InN epilayer 213 by using an electron-beam evaporation system, is preferably a structure of Au/Al/Ti (50 nm/200 nm/50 nm) and serves as a source terminal for coupling to a second voltage, wherein the second voltage is lower than the first voltage.

The catalytic layer 216, deposited between the first conductive contact 214 and the second conductive contact 215 on the InN epilayer 213 by using an electron-beam evaporation system, is preferably a platinum (Pt) layer having a thickness of around 10 nm. The catalytic layer 216 is used for enhancing the output current response in acetone detection, and the principle is specified as follows.

At the top surface of the Pt layer, a portion of hydrogen atoms dissociated from acetone molecules react with other hydrogen atoms or the pre-adsorbed oxygen atoms to form hydrogen or water molecules, respectively, and then leave the Pt layer. On the other hand, some dissociated hydrogen atoms diffuse rapidly through the Pt layer, and then trapped at the Pt/semiconductor interfaces to form an interface dipole layer, which is capable of enhancing the output current response in acetone detection.

The power supply 230 is used for providing the first voltage and the second voltage.

The measurement unit 240 is used for measuring the output current.

Figure 3:
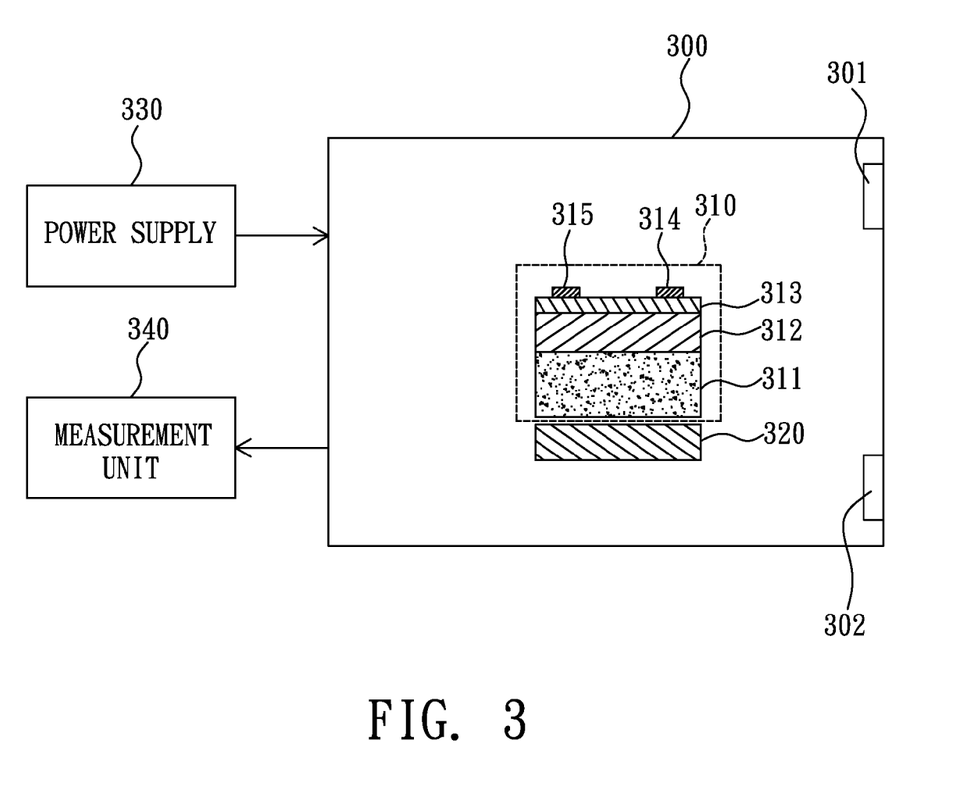
FIG. 3 is an illustrative diagram for an acetone gas sensor apparatus according to still another preferred embodiment of the present invention.

Please refer to FIG. 3, which illustrates an acetone gas sensor apparatus according to still another preferred embodiment of the present invention. As illustrated in FIG. 3, the acetone gas sensor apparatus mainly includes a chamber 300, an acetone gas sensor 310, and a heater 320, and the acetone gas sensor apparatus is powered by a power supply 330 and the measurement result is derived by a measurement unit 340.

The chamber 300 has an inlet 301 for the inflow of a breath gas, and an outlet 302 for the outflow of the gas in the chamber 300.

The acetone gas sensor 310 includes a substrate layer 311, a buffer layer 312, an InN epilayer 313, a first conductive contact 314, and a second conductive contact 315.

The substrate layer 311, preferably a c-plane sapphire layer or a (111) silicon layer having a robust surface against chemical damages, is used for depositing a gateless transistor.

The buffer layer 312, preferably an AlN layer, is deposited on the substrate layer 311 by using a plasma-assisted molecular beam epitaxy (PAMBE) system.

The InN epilayer 313, deposited on the buffer layer 312 by using a plasma-assisted molecular beam epitaxy (PAMBE) system, is used for providing a current path between the first conductive contact 314 and the second conductive contact 315 for an output current. The InN epilayer 313 can provide a surface channel, which is an ultrathin n type channel of only few nanometers near the surface of the InN epilayer 313, formed due to surface electron inversion caused by acetone gas. The InN (indium nitride) epilayer 313 preferably has a thickness of around 10 nm.

The first conductive contact 314, deposited on the InN epilayer 313 by using an electron-beam evaporation system, is preferably a structure of Au/Al/Ti (50 nm/200 nm/50 nm) and serves as a drain terminal for coupling to a first voltage.

The second conductive contact 315, deposited on the InN epilayer 313 by using an electron-beam evaporation system, is preferably a structure of Au/Al/Ti (50 nm/200 nm/50 nm) and serves as a source terminal for coupling to a second voltage, wherein the second voltage is lower than the first voltage.

The heater 320, preferably an aluminum heater placed underneath the acetone gas sensor 310, is used for heating the acetone gas sensor 310.

The power supply 330 is used for providing the first voltage and the second voltage.

The measurement unit 340 is used for measuring the output current.

Figure 5:
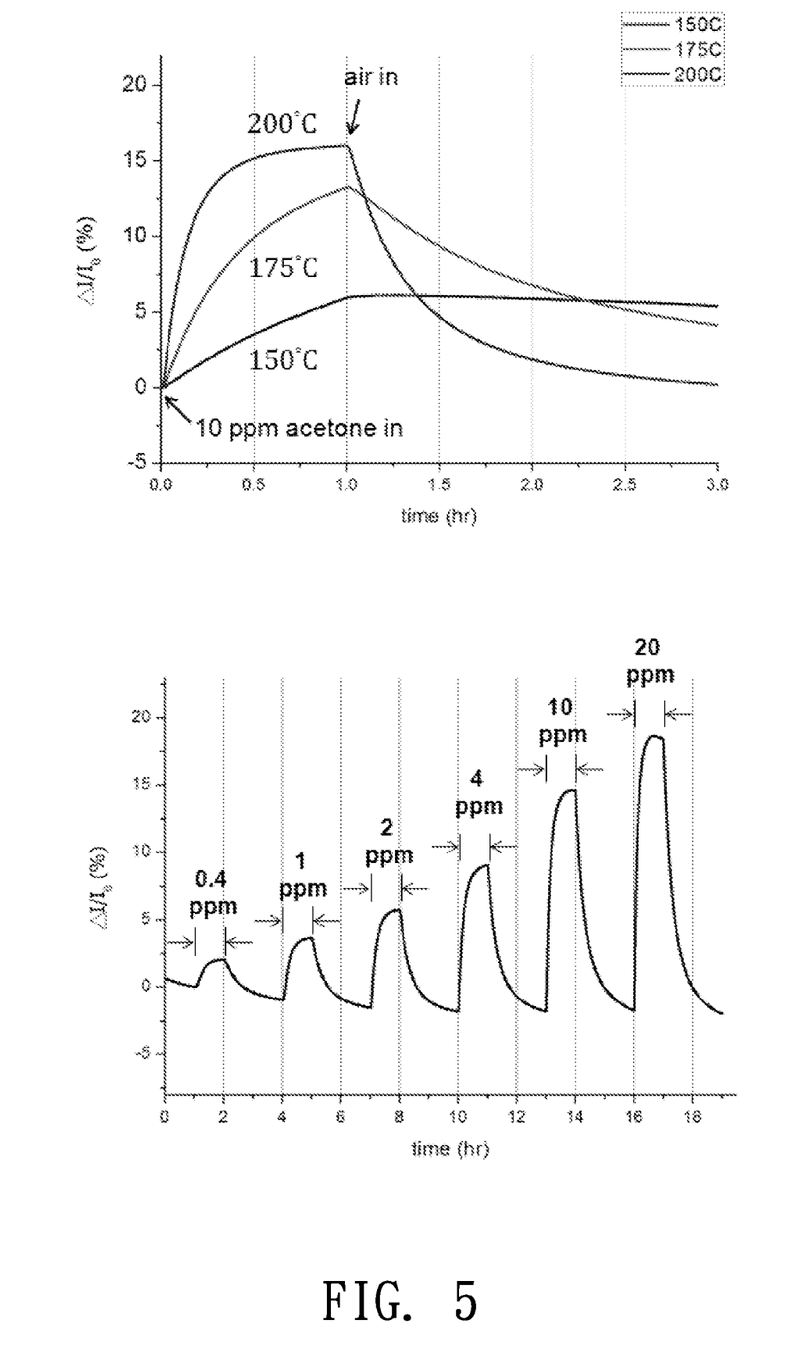
FIG. 5 illustrates responses of the output current of the acetone gas sensor apparatus in FIG. 3 under different ambient temperatures and different acetone concentrations.

FIG. 5 illustrates responses of the output current of the acetone gas sensor apparatus in FIG. 3 under different ambient temperatures and different acetone concentrations. As can be seen in FIG. 5, the response of the output current becomes faster as the ambient temperature gets higher or the acetone concentration increases. As a result, a first level—corresponding to 0.8 ppm for example—and a second level—corresponding to 1.7 ppm for example—can be used as thresholds to help diagnose diabetes. When the steady level of the output current is below the first level, it indicates "normal"; and when the steady level of the output current is above the second level, it indicates "diabetes".

Figure 4:
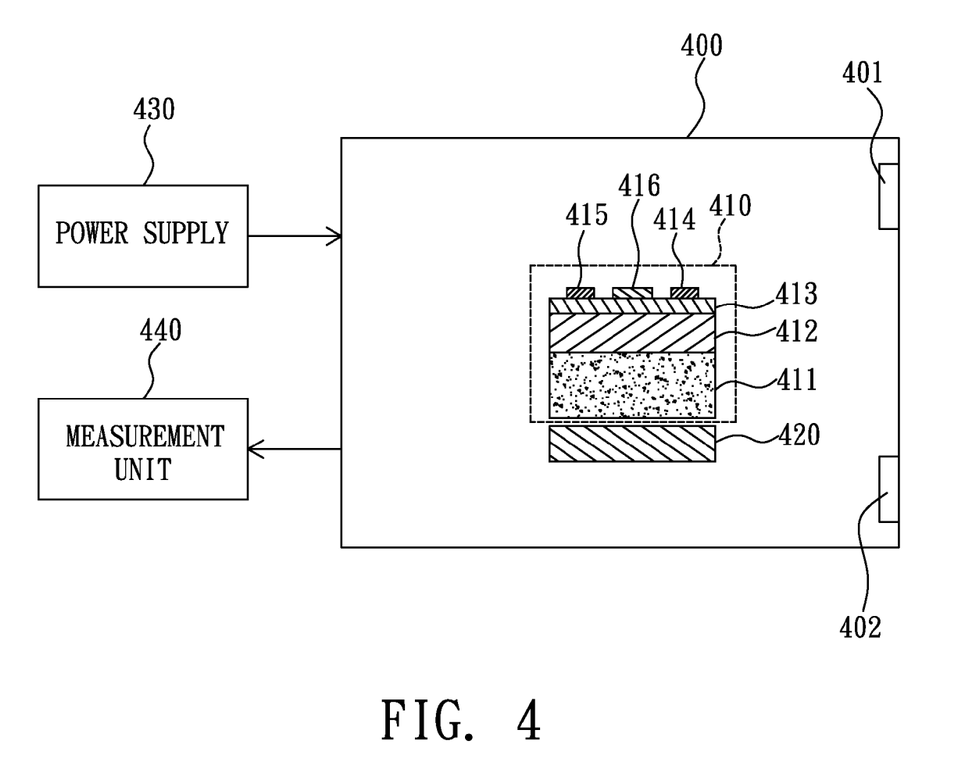
FIG. 4 is an illustrative diagram for an acetone gas sensor apparatus according to still another preferred embodiment of the present invention.

Please refer to FIG. 4, which illustrates an acetone gas sensor apparatus according to still another preferred embodiment of the present invention. As illustrated in FIG. 4, the acetone gas sensor apparatus mainly includes a chamber 400, an acetone gas sensor 410, and a heater 420, and the acetone gas sensor apparatus is powered by a power supply 430 and the measurement result is derived by a measurement unit 440.

The chamber 400 has an inlet 401 for the inflow of a breath gas, and an outlet 402 for the outflow of the gas in the chamber 400.

The acetone gas sensor 410 includes a substrate layer 411, a buffer layer 412, an InN epilayer 413, a first conductive contact 414, a second conductive contact 415, and a catalytic layer 416.

The substrate layer 411, preferably a c-plane sapphire layer or a (111) silicon layer having a robust surface against chemical damages, is used for depositing a gateless transistor.

The buffer layer 412, preferably an AlN layer, is deposited on the substrate layer 411 by using a plasma-assisted molecular beam epitaxy (PAMBE) system.

The InN epilayer 413, deposited on the buffer layer 412 by using a plasma-assisted molecular beam epitaxy (PAMBE) system, is used for providing a current path between the first conductive contact 414 and the second conductive contact 415 for an output current. The InN epilayer 413 can provide a surface channel, which is an ultrathin n type channel of only few nanometers near the surface of the InN epilayer 413, formed due to surface electron inversion caused by acetone gas. The InN (indium nitride) epilayer 413 preferably has a thickness of around 10 nm.

The first conductive contact 414, deposited on the InN epilayer 413 by using an electron-beam evaporation system, is preferably a structure of Au/Al/Ti (50 nm/200 nm/50 nm) and serves as a drain terminal for coupling to a first voltage.

The second conductive contact 415, deposited on the InN epilayer 413 by using an electron-beam evaporation system, is preferably a structure of Au/Al/Ti (50 nm/200 nm/50 nm) and serves as a source terminal for coupling to a second voltage, wherein the second voltage is lower than the first voltage.

The catalytic layer 416, deposited between the first conductive contact 414 and the second conductive contact 415 on the InN epilayer 413 by using an electron-beam evaporation system, is preferably a platinum (Pt) layer having a thickness of around 10 nm.

The heater 420, preferably an aluminum heater placed underneath the acetone gas sensor 410, is used for heating the acetone gas sensor 410.

The power supply 430 is used for providing the first voltage and the second voltage.

The measurement unit 440 is used for measuring the output current.

Figure 6:
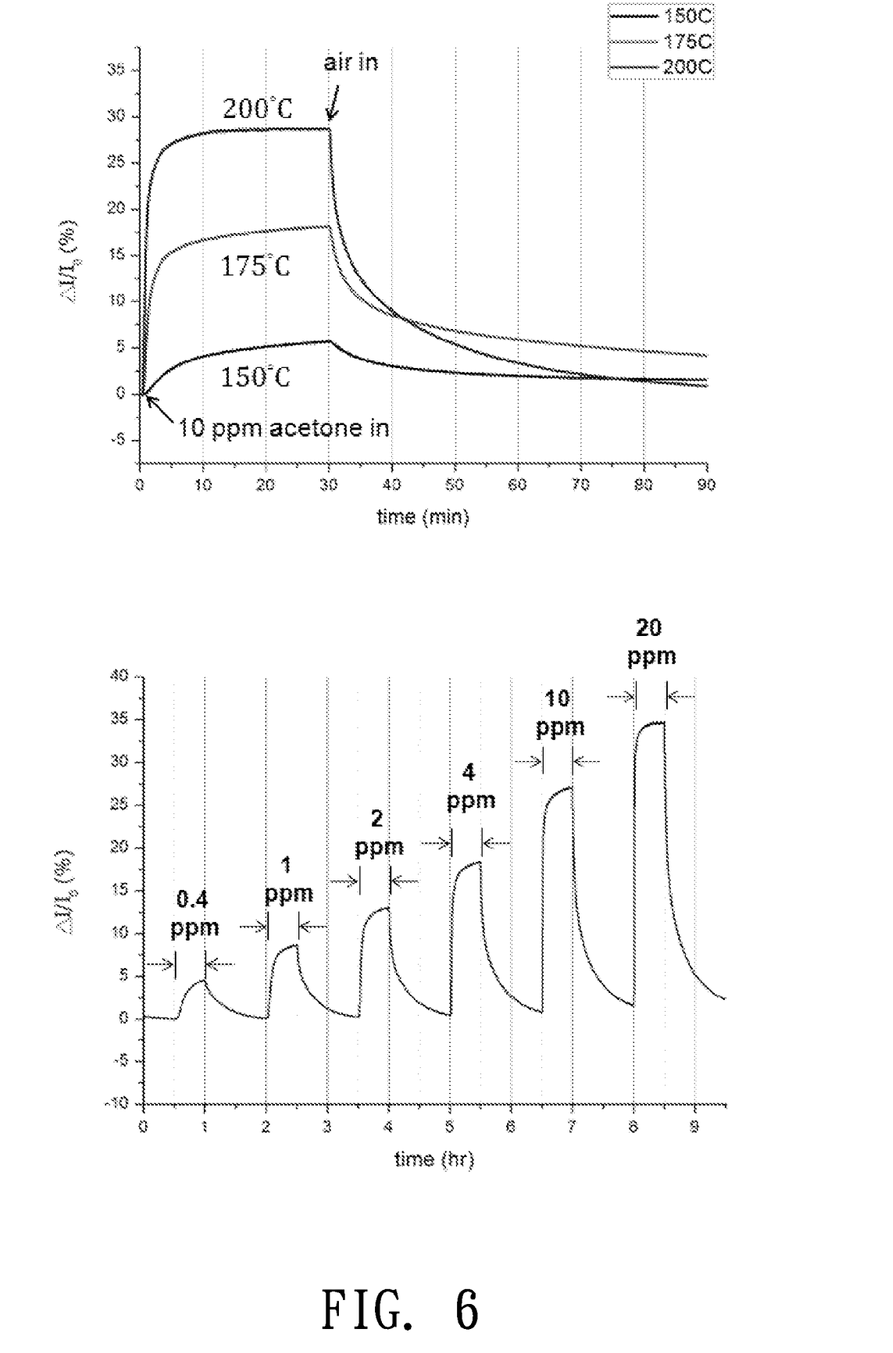
FIG. 6 illustrates responses of the output current of the acetone gas sensor apparatus in FIG. 4 under different ambient temperatures and different acetone concentrations.

FIG. 6 illustrates responses of the output current of the acetone gas sensor apparatus in FIG. 4 under different ambient temperatures and different acetone concentrations. Compared with those in FIG. 5, the responses of the output current in FIG. 6 are apparently faster and larger due to the catalytic layer 416.

In conclusion, the acetone gas sensor apparatus of the present invention possesses the following advantages:

1. The present invention has superior performance in detecting acetone in a gas sample with low acetone concentrations.

2. The present invention is capable of speeding up the acetone detection process.

3. The acetone gas sensor apparatus of the present invention can be made portable and is easy to implement.

While the invention has been described by way of example and in terms of a preferred embodiment, it is to be understood that the invention is not limited thereto. To the contrary, it is intended to cover various modifications and similar arrangements and procedures, and the scope of the appended claims therefore should be accorded the broadest interpretation so as to encompass all such modifications and similar arrangements and procedures. For example, the substrate can be silicon, r-sapphire, c-sapphire, etc.; the crystal orientation can be c-, a-, m-, etc.; and the thickness can be adjusted.

In summation of the above description, the present invention herein enhances the performance than the conventional structure and further complies with the patent application requirements and is submitted to the Patent and Trademark Office for review and granting of the commensurate patent rights.

What is claimed is:

1. In an acetone gas sensor apparatus, the improvement comprising:
   a chamber, for containing a gas sample taken from a breath of a person; and
   an acetone gas sensor, placed in said chamber for generating an output current in response to an acetone concentration of said gas sample, said acetone gas sensor comprising:
   a substrate which is a c-plane sapphire layer or a silicon layer;
   an AlN buffer layer, deposited on said substrate;
   an InN epilayer, deposited on said buffer layer for providing a current path for said output current;
   a first conductive contact, deposited on said InN epilayer for providing a drain contact; and
   a second conductive contact, deposited on said InN epilayer for providing a source contact.

2. The improvement of claim 1, wherein said first conductive contact and said second conductive contact both include a layered structure of Au/Al/Ti.

3. The improvement of claim 1, wherein said first conductive contact is used to couple to a first voltage and said second conductive contact is used to couple to a second voltage.

4. The improvement of claim 1, wherein said acetone gas sensor further comprises a catalytic layer, which is deposited, between said first conductive contact and said second conductive contact, on said InN epilayer.

5. The improvement of claim 4, wherein said catalytic layer includes platinum.

6. The improvement of claim 1, further comprising a heating device, used for heating said acetone gas sensor.

7. The improvement of claim 6, wherein said heating device is placed underneath said acetone gas sensor.

8. The improvement of claim 6, wherein said heating device is an aluminum heater.

9. In an acetone gas sensor apparatus, the improvement comprising:
　　a chamber, used for containing a gas sample taken from a breath of a person;
　　an acetone gas sensor, placed in said chamber for generating an output current in response to an acetone concentration of said gas sample;
　　a heating device, used for heating said acetone gas sensor; and
　　a measurement unit, coupled with said acetone gas sensor for providing a measured signal corresponding to said output current;
　　wherein said acetone gas sensor comprising:
　　a substrate which is a c-plane sapphire layer or a silicon layer;
　　an AlN buffer layer, deposited on said substrate;
　　an InN epilayer, deposited on said buffer layer for providing a current path for said output current;
　　a first conductive contact, deposited on said InN epilayer for providing a drain contact, which is coupled to a first voltage; and
　　a second conductive contact, deposited on said InN epilayer for providing a source contact, which is coupled to a second voltage.

10. The acetone gas sensor apparatus as disclosed in claim 9, wherein said first conductive contact and said second conductive contact both include a layered structure of Au/Al/Ti.

11. The improvement of claim 9, wherein said acetone gas sensor further comprises a catalytic layer, which is deposited, between said first conductive contact and said second conductive contact, on said InN epilayer.

12. The improvement of claim 11, wherein said catalytic layer includes platinum.

13. The improvement of claim 9, wherein said heating device is placed underneath said acetone gas sensor.

14. The improvement of claim 9, wherein said heating device is an aluminum heater.

15. In an acetone gas sensor apparatus for diabetes detection, the improvement comprising:
　　a chamber, for containing a gas sample taken from a breath of a person;
　　an acetone gas sensor placed in said chamber for generating an output current in response to an acetone concentration of said gas sample;
　　a heating device, for heating said acetone gas sensor; and
　　a measurement unit coupled with said acetone gas sensor for providing a measured signal corresponding to said output current for diabetes diagnosis;
　　wherein said acetone gas sensor comprising:
　　a substrate which is a c-plane sapphire layer or a silicon layer;
　　an AlN buffer layer, deposited on said substrate;
　　an InN epilayer, deposited on said buffer layer for providing a current path for said output current;
　　a first conductive contact, deposited on said InN epilayer for providing a drain contact, which is coupled to a first voltage;
　　a second conductive contact, deposited on said InN epilayer for providing a source contact, which is coupled to a second voltage; and
　　a catalytic layer, which is deposited, between said first conductive contact and said second conductive contact, on said InN epilayer.

16. A non-invasive test method using the acetone gas sensor apparatus of claim 15 to monitor and measure human breath whereby a user may test for and detect an abnormal concentration of acetone in the human breath, acetone being a biomarker for early detection of diabetes, the method comprising:
　　introducing a sample of exhaled breath from the user into the chamber,
　　heating the sample of exhaled breath in the chamber, and
　　sensing and measuring an output signal generated by the heated sample of exhaled breath,
　　whereby if the measured output signal is below a predetermined first level of acetone concentration the user is diagnosed as normal and if the signal is above a predetermined second level of acetone concentration, which is higher than the first level of acetone concentration, the user is diagnosed with diabetes.

17. The method of claim 16, wherein the predetermined first level of acetone concentration is approximately 0.8 ppm and the predetermined second level of acetone concentration is in the rand of about 1.7 and 3.7 ppm.

* * * * *